US006405863B1

(12) United States Patent
Dhindsa

(10) Patent No.: US 6,405,863 B1
(45) Date of Patent: Jun. 18, 2002

(54) SURGICAL INSTRUMENT TRAY AND SYSTEM

(76) Inventor: Avtar S. Dhindsa, 3305 Greyfox Dr., Valparaiso, IN (US) 46383

(*) Notice: Subject to any disclaimer, the term of this patent is extended or adjusted under 35 U.S.C. 154(b) by 0 days.

(21) Appl. No.: 09/761,612

(22) Filed: Jan. 17, 2001

(51) Int. Cl.[7] .............................................. B65D 83/10
(52) U.S. Cl. ...................................... 206/370; 206/438
(58) Field of Search ................................. 206/349, 363, 206/364, 370, 378, 438, 564, 571; 108/25, 26; 211/60.1

(56) References Cited

U.S. PATENT DOCUMENTS

| | | | |
|---|---|---|---|
| 3,013,656 A | 12/1961 | Murphy, Jr. | |
| 4,046,254 A | 9/1977 | Kramer | |
| 4,153,160 A | 5/1979 | Leigh | |
| 4,160,505 A * | 7/1979 | Rauschenberger | 206/571 |
| 4,523,679 A * | 6/1985 | Paikoff et al. | 206/370 |
| 4,595,102 A | 6/1986 | Cianci et al. | |
| 5,131,537 A * | 7/1992 | Gonzales | 206/564 |
| 5,275,281 A * | 1/1994 | Ebeling | 206/564 |
| 5,381,896 A | 1/1995 | Simons | |
| 5,394,983 A | 3/1995 | Latulippe et al. | |
| 5,441,152 A | 8/1995 | Estes | |
| 6,012,577 A | 1/2000 | Lewis et al. | |
| 6,012,586 A | 1/2000 | Misra | |
| 6,070,732 A * | 6/2000 | Chen | 206/378 |
| 6,216,885 B1 * | 4/2001 | Guillaume | 206/564 |

* cited by examiner

Primary Examiner—Luan K. Bui
(74) Attorney, Agent, or Firm—Brinks Hofer Gilson & Lione

(57) ABSTRACT

A system for organizing a set of surgical instruments for an endoscopic surgical procedure includes a tray body that defines a set of recesses. Some of the recesses are each designed to receive the operating portion of a respective endoscopic surgical instrument. These recesses are notched at one side such that the elongated invasive portions of the endoscopic surgical instruments are positioned entirely or partially outside of the tray body, directly supported by the same table surface that supports the tray body during an endoscopic procedure.

17 Claims, 4 Drawing Sheets

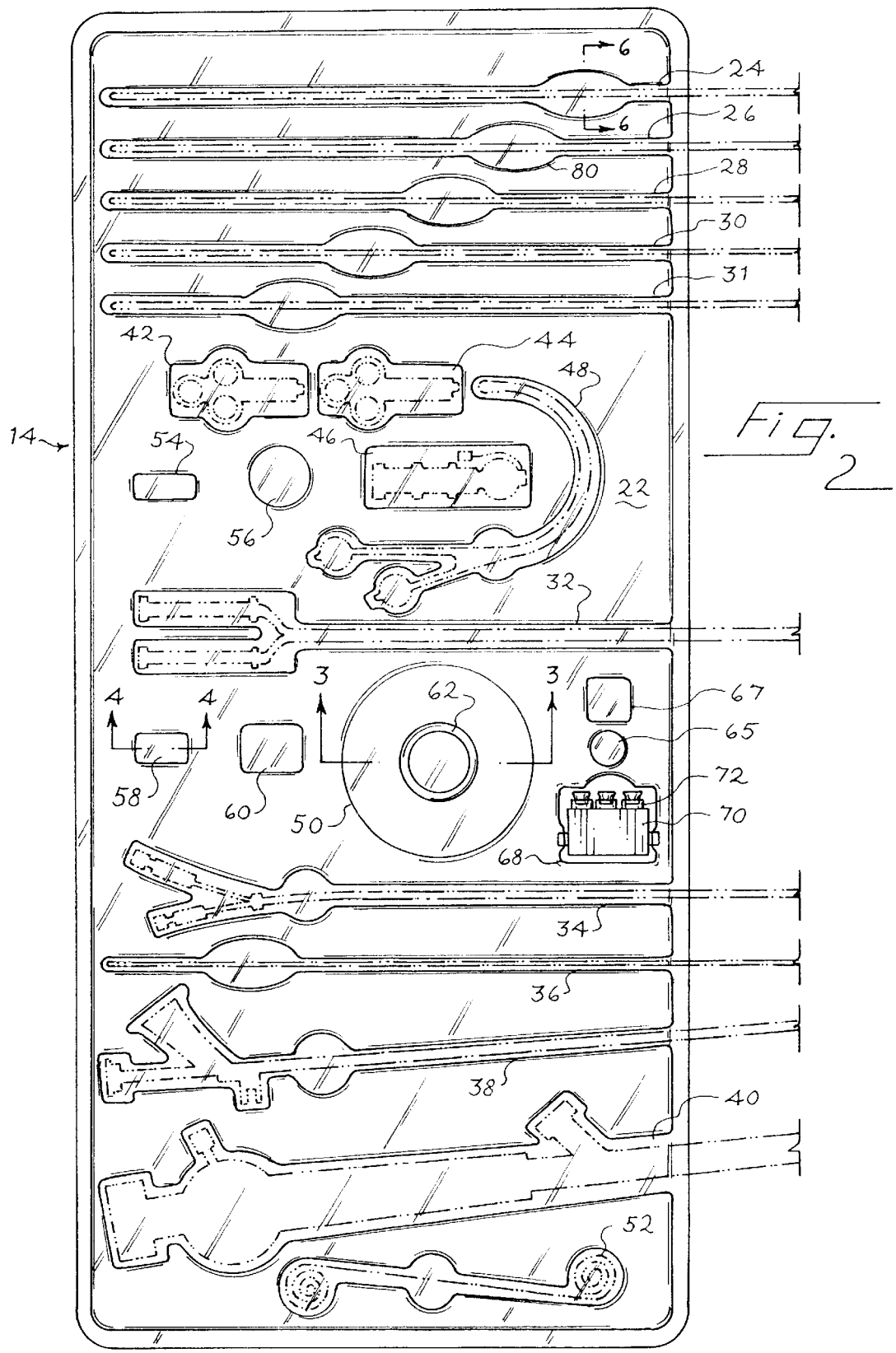

SURGICAL INSTRUMENT TRAY AND SYSTEM

BACKGROUND

The present invention relates to systems for organizing a set of surgical instruments during an endoscopic surgical procedure.

Endoscopic surgical procedures such as ureteroscopy procedures are performed with an endoscope such as a ureteroscope and associated accessories. Typically, there are at least seven or eight accessory instruments that are used whenever a ureteroscopy procedure is performed.

When the surgical instruments for ureteroscopy are simply arranged on a table, there is a tendency for the instruments to become disordered during the surgical procedure. In some cases, instruments have become contaminated or have fallen off of the support table during the procedure.

Various organizing trays have been proposed in the past for surgical instruments, including the trays described in Estes U.S. Pat. No. 5,441,152, Misra U.S. Pat. No. 6,012,586, Murphy U.S. Pat. No. 3,013,656, Kramer U.S. Pat. No. 4,046,254, Leigh U.S. Pat. No. 4,153,160, and Cianci U.S. Pat. No. 4,595,102. However, the trays disclosed in these patents are not well adapted for use with ureteroscopic surgical instruments, because of the highly elongated shape of such instruments.

BRIEF SUMMARY

The preferred embodiment described below includes a tray body that defines a number of recesses. Selected ones of these recesses are shaped to receive and organize the operating portions of respective endoscopic instruments. These recesses each include a respective notch configured to pass the invasive portion of the respective endoscopic instrument to a region alongside the tray body.

In use, the operating portions of the endoscopic instruments are positioned within the recesses of the tray body, while the elongated invasive portions pass outside of the tray body and are supported by the adjacent support surface, typically a table covered with a sterile paper.

The embodiment described below provides the advantage that the tray body itself is much smaller than the endoscopic instruments stored in the tray body. Nevertheless, the tray body still organizes the instruments in a convenient and predictable array throughout the surgical procedure.

The foregoing paragraphs have been provided by way of general introduction, and they should not be used to narrow the scope of the following claims.

BRIEF DESCRIPTION OF THE DRAWINGS

FIG. 2 is an enlarged top view of the tray of FIG. 1, showing the surgical instruments in dotted lines.

DETAILED DESCRIPTION OF THE PRESENTLY PREFERRED EMBODIMENTS

Figure 1:
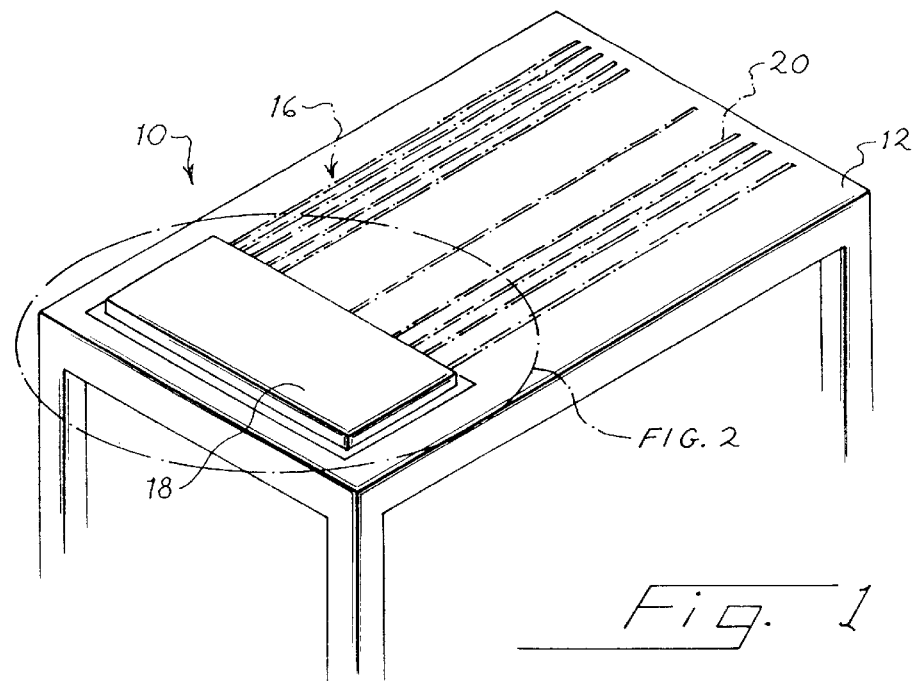
FIG. 1 is a perspective view of a set of surgical instruments positioned in tray that incorporates a preferred embodiment of this invention. The circled region of FIG. 1 is shown in detail in FIG. 2.

Turning now to the drawings, FIG. 1 shows a perspective view of a table 10 having an upper surface 12 that supports a tray 14 and a set of surgical instruments 16. The table 10 may, for example, be positioned within an operating room, and the surface 12 may be covered with a sterile sheet of a suitable material such as paper. The tray 14 organizes the surgical instruments 16 and holds them in predetermined positions during the surgical procedure. As described in greater detail below, certain of the surgical instruments 16 include operating portions that are supported by the tray 14 (that is in turn supported by a first portion of the support surface 12) and elongated invasive portions 20 that extend outside of the tray 14 and are supported directly by a second portion of the support surface 12. FIG. 1 is partially schematic, in that the details of the tray 14 and the operating portions are not shown. However, these details are clearly shown in FIG. 2.

FIG. 2 shows an enlarged view of the tray 14. As shown in FIG. 2, the tray includes a tray body 22 that defines an array of recesses that are open upwardly.

The recesses of the tray body 22 can be considered in two groups. The recesses of the first group are shaped to receive and hold respective endoscopic surgical instruments. The recesses of this first group are numbered 24–40, and they are in this example shaped to receive the endoscopic surgical instruments listed in Table 1.

TABLE 1

| Recess | Endoscopic Surgical Instrument |
| --- | --- |
| 24, 26, 28, 30 | Ureteral catheters |
| 31 | Ureteral cytology brush |
| 32 | Stone extraction baskets |
| 34 | Double lumen catheter |
| 36 | Ureteroscope sheath |
| 38 | Ureteroscope (rigid) |
| 40 | Ureteroscope (flexible) |

For example, the ureteral catheters 24, 26, 28, 30 may include cone-tip, whistle-tip, angled (Kumpe), and open-ended catheters.

Figure 5:
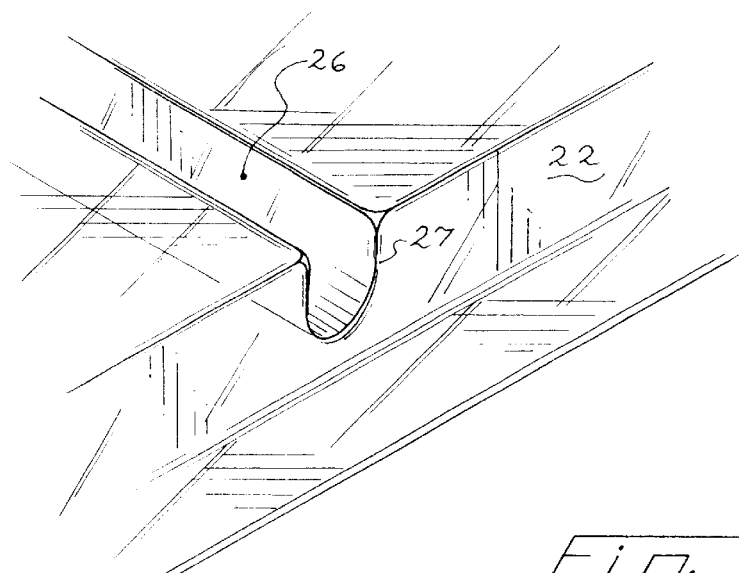
FIG. 5 is a fragmentary side perspective view of a portion of the tray of FIG. 2.

Each of these instruments includes an operating portion that is shaped to fit in and be supported by the respective recess, as well as an invasive portion that extends out the right side of the tray body 22 (in the view of FIG. 2). The operating portions of the ureteroscopes 38, 40 include the respective handpieces. FIG. 5 shows a side perspective view of a portion of the tray body 22 including the recess 26 and the associated notch 27 positioned to allow the invasive portion of a catheter within the recess 26 to exit the side of the tray body 22. Similar notches of appropriate dimensions are provided for the remaining recesses of Table 1.

The tray body 22 also defines additional recesses 42–52, in this example each sized to receive and hold a respective surgical instrument as set out in Table 2.

TABLE 2

| Recess | Surgical Instrument |
| --- | --- |
| 42, 44 | Syringe |
| 46 | Pressure syringe |
| 48 | Pressure dilation balloon |
| 50 | Guide wires |
| 52 | Stent |

Because the surgical instruments of Table 2 are relatively compact as compared with the endoscopic surgical instruments of Table 1, the recesses 42–52 do not require side-opening notches of the type described above in conjunction with Table 1 and FIG. 5.

The tray body 22 of FIG. 2 also defines various wells designed to receive and retain other surgical accessories. In the example of FIG. 2, the well 54 is sized to retain nibs, valves and other small parts useful in an endoscopic surgical procedure. The well 56 stores a contrast agent in bulk form ready for use; the well 58 stores a lubricant in bulk form ready for use; the well 60 stores a plurality of standard gauze pads; and the well 62 is designed to facilitate the collection of tissue specimens.

Figure 3:
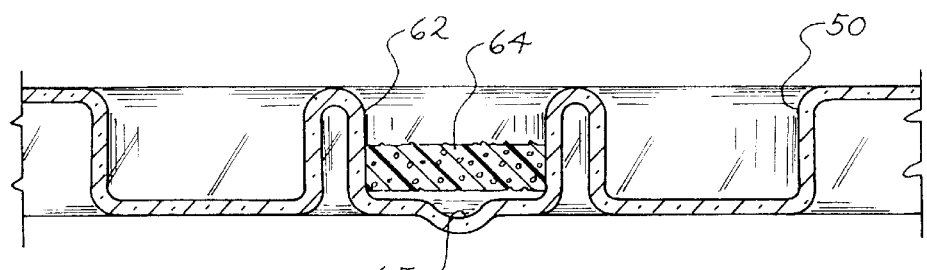
FIG. 3 is a cross-sectional view taken along line 3—3 of FIG. 2.

As shown in FIG. 3, the well 62 retains an absorbent pad 64 and includes a further recess 65 for collecting liquids. During a surgical procedure, tissue samples can be placed on the absorbent pad 64, and the collected specimens can drain into the pad 64 until they are removed from the well 62 for storage or analysis.

Figure 4:
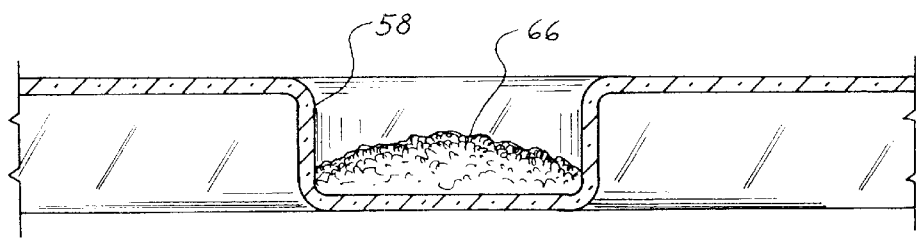
FIG. 4 is a cross-sectional view taken along line 4—4 of FIG. 2.

FIG. 4 shows a cross-sectional view through the lubricant well 58 showing the bulk lubricant 66. As used herein, the term "bulk" is intended to refer to a material that is contained within the respective well without additional packaging or containers.

The well 65 is shaped to hold a urine cup for urine cytology samples. The well 67 is intended as a rinsing well. A suitable rinsing liquid can be placed in the rinsing well to allow brushes and baskets to be cleaned as needed.

Figure 8:
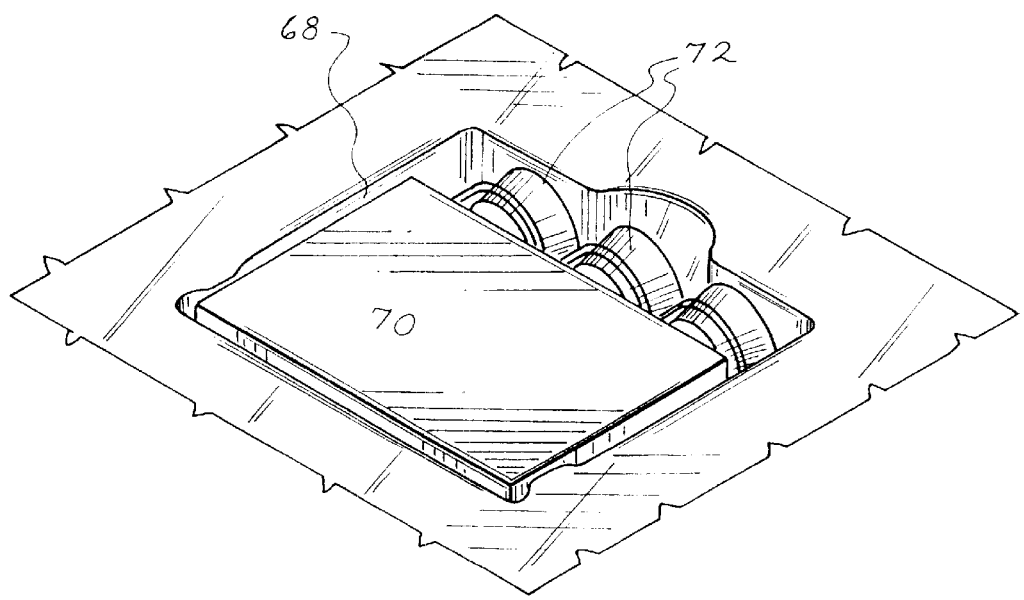
FIG. 8 is a view corresponding to that of FIG. 7 showing the container rack rotated to a lowered position.
Figure 7:
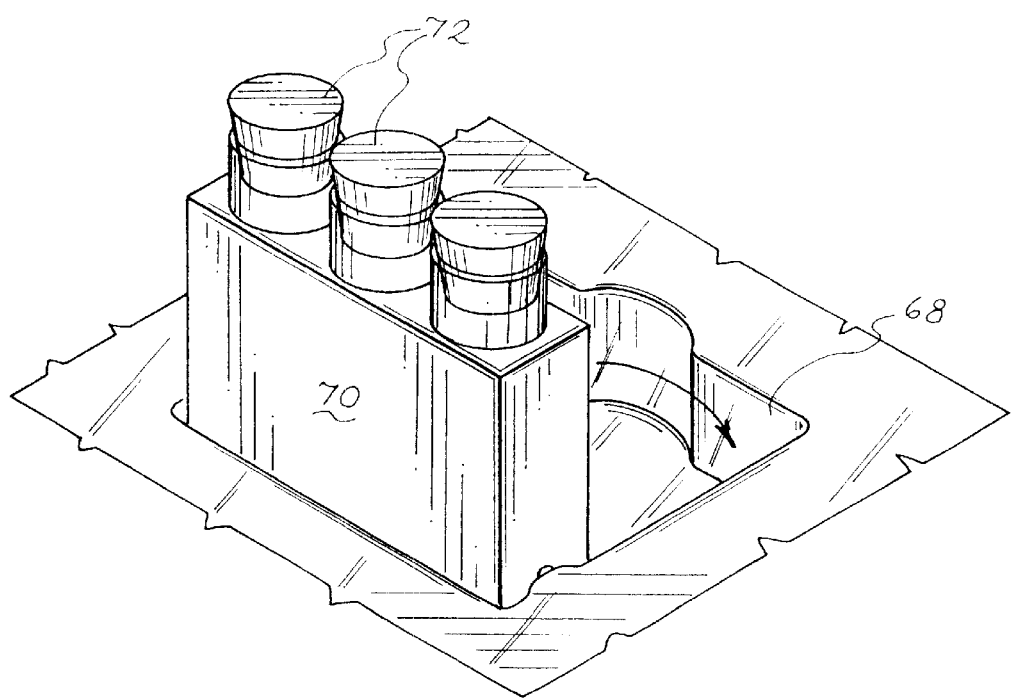
FIG. 7 is a perspective view showing a container rack of the tray of FIG. 2 rotated to a raised position.

The tray 14 also includes a pocket 68 that supports a rack 70 that in turn removably supports a set of containers 72. In this example, the containers are stoppered test tubes, and there are three of the containers 72 in the rack 70. Of course, the containers may be configured differently, and more or fewer containers may be carried by the rack 70. FIG. 7 shows the rack 70 rotated in the tray body to a raised position, in which the containers 72 extend out of the associated pocket 68 in the tray 14. FIG. 8 shows the rack 70 rotated in the tray body to a lowered position, in which the rack 70 and the containers 72 are received within the associated pocket 68 in the tray 14. The containers 72 are useful in collecting upper tract cytology samples for later analysis.

Figure 6:
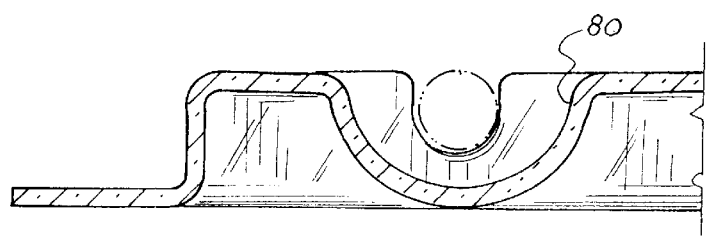
FIG. 6 is a cross-sectional view taken along line 6—6 of FIG. 2.

As shown in FIG. 2 and more clearly in FIG. 6, many of the recesses of Tables 1 and 2 are provided with enlarged regions that allow a physician to insert a finger on either side of the surgical instrument within the recess. This facilitates removal of surgical instruments from the recesses and replacement of surgical instruments back into the recesses. In FIG. 6, the enlarged region is indicated by the reference number 80.

The tray 14 is preferably formed of a lightweight, inexpensive material that can readily be sterilized for reuse or alternatively that can be discarded after a single use. For example, the tray 14 can be thermoformed from sheet plastic material. In this case, the region between adjacent recesses may be positioned either at a relatively high level (as shown in FIGS. 3, 4, 5 and 6), or alternately at a low level in contact with the support surface. In the later case, the recesses are defined by upstanding ridges, similar to the ridges that define the well 62 of FIG. 3.

It should be apparent from the foregoing description that the system of this invention provides substantial advantages during an endoscopic surgical procedure. The surgical instruments needed for the procedure are organized in a well-controlled and consistent pattern. This makes it easier for the physician to locate a required surgical instrument quickly without the assistance of a trained or a specialized surgical nurse. Surgical instruments are prevented from becoming entangled or misplaced during the surgical procedure, and the incidence of contamination should to be substantially reduced.

Furthermore, the tray 14 is relatively small in that the recesses for the endoscopic surgical instruments receive the operating portions but not the entire invasive portions of the endoscopic instruments. Part of each invasive portion can be received in each respective recess, but not the entire length of the respective endoscopic instrument. Similarly, part (but not all) of each operating portion can extend outside of the tray via the respective notch. Because of the notches described above, the invasive portions of the endoscopic instruments are supported in part directly by the support surface, thereby reducing the size and cost of the tray.

Of course, many changes and modifications can be made to the preferred embodiment described above. Recesses may be provided for more, fewer, or different surgical instruments than those illustrated in FIG. 2. Any suitable material can be used to form the tray 14, using any suitable forming method. The relative positions and proportions of the various recesses can be altered as appropriate for the particular surgical procedure and the particular surgical instruments being housed in the tray. The illustrated recesses of FIG. 2 are intended only as examples. In the event that differently shaped instruments are used, the recesses of the tray can be shaped differently to fit the instruments of the particular application.

Furthermore, though this invention has been described in conjunction with ureteroscopy procedures, it should be understood that this invention can be adapted for use with other endoscopic procedures. In this case, the recesses should be modified as appropriate for the surgical instruments used in the particular endoscopic procedure.

As used herein, the term "endoscopic" is intended broadly to encompass a wide range of endoscopic procedures, including for example ureteroscopic, arthroscopic, and laparoscopic procedures.

As used herein, the term "operating portion" is intended broadly to encompass the portion of an elongated surgical instrument that is directly manipulated by the hand of the physician. Similarly, the term "invasive portion" refers to the elongated portion of an endoscopic instrument that is inserted into the body of the patient during a surgical procedure.

The foregoing detailed description has described only a few of the many forms that this invention can take. This detailed description should therefore be taken as illustrative rather than limiting. It is only the following claims, including all equivalents, that are intended to define the scope of this invention.

What is claimed is:

1. A surgical instrument system comprising:
   a tray body comprising a plurality of recesses;

first and second endoscopic instruments, each endoscopic instrument comprising a respective operating portion and a respective elongated invasive portion;

said recesses comprising first and second recesses receiving and positioning the operating portions of the first and second endoscopic instruments, respectively;

said first recess comprising a first notch passing the invasive portion of the first endoscopic instrument to a region alongside the tray body;

said second recess comprising a second notch passing the invasive portion of the second endoscopic instrument to the region alongside the tray body;

said invasive portions extended beyond the tray body and supported on a support surface alongside the tray body.

2. The invention of claim 1 wherein the tray body further comprises at least one well containing a lubricant in bulk form, and at least one additional well containing a contrast agent in bulk form.

3. The invention of claim 1 wherein the tray further comprises:

at least one specimen well; and an absorbent pad contained in the specimen well.

4. The invention of claim 1 wherein the tray further comprises:

a recessed pocket; and a container rack carrying a plurality of containers, said rack movably positioned in the recessed pocket.

5. The invention of claim 4 wherein the rack is rotatably mounted in the recessed pocket for movement between a lowered position, in which the containers are received in the recessed pocket, and a raised position, in which the containers extend out of the recessed pocket.

6. The invention of claim 1 wherein the recesses in the tray body additionally comprise recesses shaped to receive at least three surgical instruments selected from the group consisting of: a syringe, a pressure syringe, a pressure dilation balloon, a guide wire, a stent, and an absorbent pad.

7. The invention of claim 1 wherein the first and second recesses are shaped to receive respective endoscopic instruments selected from the group consisting of: a flexible ureteroscope, a rigid ureteroscope, a ureteroscope sheath, a ureteral catheter, a ureteral cytology brush, a double lumen catheter, and a stone extraction basket.

8. The invention of claim 1 wherein the recesses in the tray body additionally comprise at least two recesses selected from the group consisting of: a rinsing well, a recess for a urine cytology cup, and a recess for collecting liquids.

9. A system for organizing a set of surgical instruments for an endoscopic surgical procedure, said system comprising:

a support surface;

a tray body covering a first portion of the support surface, a second portion of the support surface exposed alongside the tray body;

said tray body comprising a plurality of recesses, each recess shaped to receive a respective surgical instrument;

a plurality of surgical instruments disposed in the recesses of the tray body, said instruments comprising first and second endoscopic instruments, each endoscopic instrument comprising a respective operating portion and a respective elongated invasive portion;

said recesses comprising first and second recesses shaped to receive and position the operating portions of the first and second endoscopic instruments, respectively;

said first recess comprising a first notch configured to pass the invasive portion of the first endoscopic instrument to a region alongside the tray body;

said second recess comprising a second notch configured to pass the invasive portion of the second endoscopic instrument to the region alongside the tray body;

said elongated invasive portions supported at least in part by the second portion of the support surface, said operating portions supported by the tray body.

10. The invention of claim 9 wherein the tray body further comprises at least one well containing a lubricant in bulk form, and at least one additional well containing a contrast agent in bulk form.

11. The invention of claim 9 wherein the tray further comprises:

at least one specimen well; and an absorbent pad contained in the specimen well.

12. The invention of claim 9 wherein the tray further comprises:

a recessed pocket; and a container rack carrying a plurality of containers, said rack movably positioned in the recessed pocket.

13. The invention of claim 12 wherein the rack is rotatably mounted in the recessed pocket for movement between a lowered position, in which the containers are received in the recessed pocket, and a raised position, in which the containers extend out of the recessed pocket.

14. The invention of claim 9 wherein the recesses in the tray body additionally comprise recesses shaped to receive at least three surgical instruments selected from the group consisting of: a syringe, a pressure syringe, a pressure dilation balloon, a guide wire, and a stent.

15. The invention of claim 9 wherein the plurality of surgical instruments comprise at least three additional surgical instruments selected from the group consisting of a syringe, a pressure syringe, a pressure dilation balloon, a guide wire, a stent, and an absorbent pad; and wherein said at least three additional surgical instruments are disposed in respectively shaped additional recesses of the tray.

16. The invention of claim 9 wherein the first and second endoscopic instruments are selected from the group consisting of: a flexible ureteroscope, a rigid ureteroscope, a ureteroscope sheath, a ureteral catheter, a ureteral cytology brush, a double lumen catheter, and a stone extraction basket.

17. The invention of claim 9 wherein the recesses in the tray body additionally comprise at least two recesses selected from the group consisting of: a rinsing well, a recess for a urine cytology cup, and a recess for collecting liquids.

\* \* \* \* \*

UNITED STATES PATENT AND TRADEMARK OFFICE
CERTIFICATE OF CORRECTION

PATENT NO.   : 6,405,863 B1
DATED        : June 18, 2002
INVENTOR(S)  : Avtar S. Dhindsa It is certified that error appears in the above-identified patent and that said Letters Patent is hereby corrected as shown below:

<u>Column 4,</u>
Line 15, delete "should to be" and substitute -- should be -- in its place.

Signed and Sealed this

Eleventh Day of February, 2003

JAMES E. ROGAN
*Director of the United States Patent and Trademark Office*